United States Patent [19]

Ansell et al.

[11] Patent Number: 5,753,613
[45] Date of Patent: May 19, 1998

[54] COMPOSITIONS FOR THE INTRODUCTION OF POLYANIONIC MATERIALS INTO CELLS

[75] Inventors: Steven Michial Ansell; Barbara Mui; Michael Hope, all of Vancouver, Canada

[73] Assignee: Inex Pharmaceuticals Corporation, Vancouver, Canada

[21] Appl. No.: 442,267

[22] Filed: May 16, 1995

Related U.S. Application Data

[62] Division of Ser. No. 316,399, Sep. 30, 1994, abandoned.

[51] Int. Cl.$^6$ .......................... A61K 37/22; C07H 21/02; C07H 21/04
[52] U.S. Cl. ...................... 514/2; 514/21; 514/43; 514/44; 424/450
[58] Field of Search .................. 514/2, 21, 43, 514/44; 424/450

[56] References Cited

U.S. PATENT DOCUMENTS

| | | | |
|---|---|---|---|
| 4,394,372 | 7/1983 | Taylor | 424/85 |
| 4,897,355 | 1/1990 | Eppstein et al. | |
| 5,171,678 | 12/1992 | Behr et al. | |
| 5,234,767 | 8/1993 | Wallach | 428/402.2 |
| 5,279,833 | 1/1994 | Rose | |
| 5,286,634 | 2/1994 | Stadler et al. | |

FOREIGN PATENT DOCUMENTS

| | | |
|---|---|---|
| 2 552 679 | 4/1985 | France |
| 2147263 | 5/1985 | United Kingdom |
| WO 91/16024 | 10/1991 | WIPO |
| WO 93/05162 | 3/1993 | WIPO |

OTHER PUBLICATIONS

Ito et al., "Synthetic Cationic Amphiphiles for Lipsome-Mediated DNA Transfection", *Biochemistry International*, 22:No. 2, p. 235 (1990).
Pinnaduwage et al., "Use of a quaternary ammonium detergent in liposome mediated DNA transfection of mouse L-cells", *Biophysica Acta* 985 pp. 33–37 (1989).
Philip, R., et al., "Cationic Liposome—Mediated Transfection of Immune Effector Cells," *J. of Liposome Research* 3(1):71–84 (1993).
Hawley–Nelson, et al., *Focus* 15(3):73 (1993).
Stomatatos, et al., *Biochemistry* 27:3917–3925 (1988).
Zhu, N., et al., *Science* 261:209–211 (1993).
Leventis, et al., *Biochem. Biophys. Acta* 1023:124 (1990).
Chang, A.C.Y., et al., *Focus*, 10:68 (1988).
Hope, M.J., et al., *Biochimica et Biophysica Acta*, 812:55–65 (1985).

Struck, D.K., et al., *Biochemistry*, 20:4093 (1981).
Woodle, M.C., et al, *Biochimica et Biophysica Acta*, 1105:193–200 (1992).
Bennett, C.F., et al., *Molecular Pharmacology*, 41:1023–1033 (1992).
Wood, P.G., *Methods in Enzymology*, 149:271–280 (1987).
Hyde, Stephen, C., et al., *Nature*, 362:250–255 (1993).
Brigham, Kenneth L., et al., *American Journal of the Medical Sciences*, 298(4):278–281 (1989).
Behr, et al., *Proc. Natl. Acad. Sci.* USA, 86:6982–6986 (Sep. 1989).
Stewart, M.J., et al., *Human Gene Therapy*, 3:267–275 (1992).
Nicolau, C., et al., *Methods in Enzymology*, 149:157–184 (1987).
Felgner, P.L., et al., *Natl. Acad. Sci.*, USA, 84:7413–7417 (Nov. 1987).
Gao, X., et al., *Biochemical and Biophysical Research Communications*, 200(3):1201–1206 (May 16, 1994).
Pickering J.G., et al., *Circulation*, 89(1):13–21 (Jan. 1994).
Kaneda, Y., et al., *Methods in Enzymology*, 221:317–327 (1993).
Thierry, A.R., et al., *Nucleic Acids Research*, 20(21):5691–5698.
Keren–Zur, M., et al., *Biochimica et Biophysica Acta*, 983:253–258 (1989).
Nicolau, C., et al., *Methods in Enzymology*, 149:157–176 (1987).
Debs, R., et al., *Am. J. Respir. Cell Mol. Biol.*, 7:406–413 (1992).
Brigham, K.L., et al., *Am. J. Respir. Cell Mol. Biol.*, 8:209–213 (1993).
Canonico, A.E., et al., *Am. J. Respir. Cell Mol. Biol.*, 10:24–29 (1994).
Mack, K.D., et al., *Am. J. Medical Sciences*, 307(2):138–143 (Feb. 1994).
Farhood, H., et al., *Annals New York Academy of Sciences*, 716:23–35 (1994).

*Primary Examiner*—Nathan M. Nutter
*Attorney, Agent, or Firm*—Townsend and Townsend and Crew

[57] ABSTRACT

The present invention provides compositions and methods which are useful for the introduction of polyanionic materials into cells. The compositions are mixtures of cationic compounds and neutral lipids which are typically formulated as liposomes. The cationic compounds are quaternary ammonium compounds wherein the nitrogen has two attached long chain alkyl groups, at least one of which is unsaturated. The methods for transfecting cells involve (a) contacting the polyanionic materials with the compositions above to form a polyanionic material-liposome complex, and (b) contacting the complex with the cells to be transfected.

4 Claims, 4 Drawing Sheets

COMPOSITIONS FOR THE INTRODUCTION OF POLYANIONIC MATERIALS INTO CELLS

This is a Division of application Ser. No. 08/316,399 filed Sep. 30, 1994 and now abandoned.

BACKGROUND OF THE INVENTION

Gene therapy is an area of current interest which involves the introduction of genetic material into a cell to facilitate expression of a deficient protein. There are currently five major methods by which this is accomplished, namely: (i) calcium phosphate precipitation, (ii) DEAE-dextran complexes, (iii) electroporation, (iv) cationic lipid complexes and (v) reconstituted viruses or virosomes (see Chang, et al., *Focus* 10:88 (1988)). Cationic lipid complexes are presently the most effective generally used means of effecting transfection.

A number of different formulations incorporating cationic lipids are commercially available, namely (i) lipofectin (which uses 1,2-dioleyloxy-3-(N,N,N-trimethylamino) propane chloride, or DOTMA, see Eppstein, et al., U.S. Pat. No. 4,897,355); lipofectamine (uses DOSPA, see Hawley-Nelson, et al., *Focus* 15(3):73 (1993)); and lipofectAce (uses N,N-distearyl-N,N-dimethylammonium bromide, or DDAB, see Rose, U.S. Pat. No. 5,279,833). Other researchers have reported alternative cationic lipids that work in essentially the same manner but with different efficiencies, for example 1,2-dioleoyloxy-3(N,N,N-trimethylamino) propane chloride, or DOTAP, see Stomatatos, et al., *Biochemistry* 27:3917-3925 (1988)); glycerol based lipids (see Leventis, et al., *Biochem. Biophys. Acta* 1023:124 (1990); lipopolyamines (see, Behr, et al., U.S. Pat. No. 5,171,678) and cholesterol based lipids (see Epand, et al., WO 93/05162).

Others have noted that DOTMA and related compounds are significantly more active in transfection assays than their saturated analogues (see, Felgner, et al., WO91/16024). However, both DOTMA and DOSPA based formulations, despite being the most efficient of the cationic lipids in effecting transfection, are prohibitively expensive. DDAB on the other hand is inexpensive and readily available from chemical suppliers but is less effective than DOTMA in most cell lines.

What is needed in the art are new compositions and methods which are both more effective at transfection and more affordable. Surprisingly, the present invention provides such compositions and methods.

SUMMARY OF THE INVENTION

The present invention provides compositions and methods which are useful for the introduction of polyanionic materials into cells. The compositions are mixtures of cationic compounds and neutral lipids which are typically formulated as liposomes. The cationic compounds are quaternary ammonium compounds wherein the nitrogen has two attached long chain alkyl groups, at least one of which is unsaturated. The methods for transfecting cells involve (a) contacting the polyanionic materials with a liposomal formulation of the above compositions to generate a complex, and (b) contacting the complex with the cells to be transfected.

DETAILED DESCRIPTION OF THE INVENTION

Abbreviations and Definitions

The following abbreviations are used herein: BHK, baby hamster kidney; RBC, red blood cells; DDAB, N,N-distearyl-N,N-dimethylammonium bromide; DODAC, N,N-dioleyl-N,N-dimethylammonium chloride; DOPE, 1,2-sn-dioleoylphoshatidyethanolamine; DOSPA, 2,3-dioleyloxy-N-(2(sperminecarboxamido)ethyl)-N,N-dimethyl-1-propanaminium trifluoroacetate; DOTAP, 1,2-dioleoyloxy-3(N,N,N-trimethylamino)propane chloride; DOTMA, 1,2-dioleyloxy-3-(N,N,N-trimethylamino)propane chloride; OSDAC, N-oleyl-N-stearyl-N,N-dimethylammonium chloride; RT, room temperature; HEPES, 4-(2-hydroxyethyl)-1-piperazineethanesulfonic acid; FBS, fetal bovine serum; DMEM, Dulbecco's modified Eagle's medium; PBS, phosphate-buffered saline; EGTA, ethylenebis (oxyethylenenitrilo)-tetraacetic acid; SF-DMEM, serum-free DMEM; and NP40, nonylphenoxypolyethoxyethanol.

As used herein, the term "alkyl" refers to a saturated hydrocarbon radical which may be straight-chain or branched-chain (for example, methyl, ethyl, propyl, isopropyl). Preferred alkyl groups for some substituents are lower alkyl groups containing 1 to 3 carbon atoms. For other alkyl group substituents, long chain alkyl groups containing from 16 to 20 carbon atoms are preferred. All numerical ranges in this specification and claims are intended to be inclusive of their upper and lower limits.

The term "acyl" refers to a radical produced from an organic acid by removal of the hydroxyl group. Examples of acyl radicals include acetyl, pentanoyl, palmitoyl, stearoyl, myristoyl, caproyl and oleoyl.

As used herein, the term "pharmaceutically acceptable anion" refers to anions of organic and inorganic acids which provide non-toxic salts in pharmaceutical preparations. Examples of such anions include chloride, bromide, sulfate, phosphate, acetate, benzoate, citrate, glutamate, and lactate. The preparation of pharmaceutically acceptable salts is described in Berge, et al., *J. Pharm. Sci.* 66:1–19 (1977), incorporated herein by reference.

As used herein, the term "polyanion" refers to materials having more than one anionic group. For example, polyanion is used to refer to nucleic acids, both DNA and RNA which are present in their polyanionic form having more than one anionic phosphodiester group along the nucleic acid backbone. The term "polyanion" also refers to those pharmaceutical agents which have more than one anionic group at neutral pH. Such pharmaceutical agents include peptides having multiple carboxylic acid functionalities present (i.e., Glu, Asp).

The term "neutral lipid" refers to any of a number of lipid species which exist in an uncharged or neutral zwitterionic form at physiological pH. Such lipids include, for example diacylphosphatidylcholine, diacylphosphatidylethanolamine, ceramide, sphingomyelin, cephalin, cardiolipin, and cerebrosides.

The terms "transfection" and "transformation" are used herein interchangeably, and refer to the introduction of polyanionic materials, particularly nucleic acids, into cells. The term "lipofection" refers to the introduction of such materials using liposome complexes. The polyanionic materials can be in the form of DNA or RNA which is linked to expression vectors to facilitate gene expression after entry into the cell. Thus the polyanionic material used in the present invention is meant to include DNA having coding sequences for structural proteins, receptors and hormones, as well as transcriptional and translational regulatory elements (i.e., promoters, enhancers, terminators and signal sequences) and vectors. Methods of incorporating particular nucleic acids into expression vectors are well known to those of skill in the art, but are described in detail in, for example, Sambrook et al., *Molecular Cloning: A Laboratory Manual* (2nd ed.), Vols. 1–3, Cold Spring Harbor Laboratory, (1989) or *Current Protocols in Molecular Biology*, F. Ausubel et al., ed. Greene Publishing and Wiley-Interscience, New York (1987), both of which are incorporated herein by reference.

"Expression vectors", "cloning vectors", or "vectors" are often plasmids or other nucleic acid molecules that are able to replicate in a chosen host cell. Expression vectors may replicate autonomously, or they may replicate by being inserted into the genome of the host cell, by methods well known in the art. Vectors that replicate autonomously will have an origin of replication or autonomous replicating sequence (ARS) that is functional in the chosen host cell(s). Often, it is desirable for a vector to be usable in more than one host cell, e.g., in *E. coli* for cloning and construction, and in a mammalian cell for expression.

Detailed Description

The present invention provides compositions and methods for the introduction of polyanionic materials into cells. The compositions comprise a cationic compound of formula I and at least one neutral lipid.

In formula I, $R^1$ and $R^2$ are each independently $C_1$ to $C_3$ alkyl. Y and Z are alkyl or alkenyl chains and are each independently $-CH_2CH_2CH_2CH_2CH_2-$, $-CH=CHCH_2CH_2CH_2-$, $-CH_2CH=CHCH_2CH_2-$, $-CH_2CH_2CH=CHCH_2-$, $-CH_2CH_2CH_2CH=CH-$, $-CH=CHCH=CHCH_2-$, $-CH=CHCH_2CH=CH-$, or $-CH_2CH=CHCH=CH-$, with the proviso that Y and Z are not both $-CH_2CH_2CH_2CH_2CH_2-$. The letters n and q denote integers of from 3 to 7, while the letters m and p denote integers of from 4 to 9, with the proviso that the sums n+m and q+p are each integers of from 10 to 14. The symbol $X^-$ represents a pharmaceutically acceptable anion. In the above formula, the orientation of the double bond is not critical, however the cis isomers are generally preferred.

In one group of preferred embodiments, the cationic compounds are of formula I, wherein $R^1$ and $R^2$ are methyl and Y and Z are each independently $-CH=CHCH_2CH_2CH_2-$, $-CH_2CH=CHCH_2CH_2-$, $-CH_2CH_2CH=CHCH_2-$ or $-CH_2CH_2CH_2CH=CH-$. In particularly preferred embodiments of the present invention, $R^1$ and $R^2$ are methyl; Y and Z are each $-CH=CHCH_2CH_2CH_2-$; n and q are both 7; and m and p are both 5. In the most preferred embodiment, the cationic compound is DODAC (N,N-dioleyl-N,N-dimethylammonium chloride). DODAC is a known compound that has been used extensively as an additive in detergents and shampoos. There is also a report of its use as a colipid in liposomal compositions with other detergents (see, Takahashi, et al., GB 2147243).

The neutral lipids which are part of the present compositions are not critical and can be any of a variety of neutral lipids which are typically used in detergents, or for the formation of micelles or liposomes. Examples of neutral lipids which are useful in the present compositions are diacylphosphatidylcholine, diacylphosphatidylethanolamine, ceramide, sphingomyelin, cephalin, cardiolipin, and cerebrosides. In preferred embodiments, the present compositions will include one or more neutral lipids which are diacylphosphatidylcholine, diacylphosphatidylethanolamine, ceramide or sphingomyelin. The acyl groups in these neutral lipids are preferably acyl groups derived from fatty acids having $C_{10}$–$C_{24}$ carbon chains. More preferably the acyl groups are lauroyl, myristoyl, palmitoyl, stearoyl or oleoyl. In particularly preferred embodiments, the neutral lipid will be 1,2-sn-dioleoylphosphatidylethanolamine.

The anion, $X^-$, can similarly be any of a variety a pharmaceutically acceptable anions. These anions can be organic or inorganic, including for example, $Br^-$, $Cl^-$, $F^-$, $I^-$, sulfate, acetate and nitrate. In preferred embodiments, $X^-$ is $Cl^-$ or $AcO^-$.

In the compositions of the present invention, the ratio of cationic compound to neutral lipid is not critical but will be within a range of from about 25:75 (cationic compound:neutral lipid) to 75:25 (cationic compound:neutral lipid), preferably about 50:50.

The cationic compounds which are used in the above compositions can be prepared by methods known to those of skill in the art using standard synthetic reactions (see March, *Advanced Organic Chemistry*, 4th Ed., Wiley-Interscience, New York, N.Y. (1992), incorporated herein by reference). For example, the synthesis of OSDAC can be carried out by first treating oleylamine with formaldehyde and sodium cyanoborohydride under conditions which result in the reductive alkylation of the amine. This provides dimethyl oleylamine, which can then be alkylated with stearyl bromide to form the corresponding ammonium salt. Anion exchange results in the formation of OSDAC. For cationic compounds in which both fatty acid chains are unsaturated (i.e., DODAC), the following general procedure can be used. An unsaturated acid (i.e., oleic acid) can be converted to its corresponding acid chloride with such reagents as oxalyl chloride, thionyl chloride, $PCl_3$ or $PCl_5$. The acid chloride can be treated with an unsaturated amine (i.e., oleylamine) to provide the corresponding amide. Reduction of the amide with, for example, lithium aluminum hydride provides a secondary amine wherein both alkyl groups are unsaturated long chain alkyl groups. The secondary amine can then be treated with alkyl halides such as methyl iodide to provide a quaternary ammonium compound. Anion exchange can then be carried out to provide cationic compounds having the desired pharmaceutically acceptable anion.

In one group of embodiments, the pharmaceutical compositions of the present invention will be formulated as micelles or liposomes.

Micelles containing the cationic compounds and neutral lipids of the present invention can be prepared by methods which are well known to one of skill in the art. In addition to the micellar formulations of the present compositions, the present invention also provides micellar formulations which include other species such as lysophosphatidylcholine, lysophosphatidylethanolamine, lysophosphatidylserine, lysophosphatidylglycerol, phosphatidylethanolamine-polyoxyethylene conjugate, ceramide-polyoxyethylene conjugate or phosphatidic acid-polyoxyethylene conjugate. The polyoxyethylene conjugates which are used in the compositions of the present invention can be prepared by combining the conjugating group (i.e. phosphatidic acid or phosphatidylethanolamine) with an appropriately functionalized polyoxyethylene derivative. For example, phosphatidylethanolamine can be combined with polyoxyethylene bis(p-toluenesulfonate) to provide a phosphatidylethanolamine-polyoxyethylene conjugate. See, Woodle, et al., *Biochim. Biophys. Acta* 1105:193-200 (1992), incorporated herein by reference.

Liposomes can also be formed from the cationic compounds and neutral lipids of the present pharmaceutical compositions. The selection of neutral lipids is generally guided by consideration of, e.g., liposome size and stability of the liposomes in the bloodstream.

As noted above, the neutral lipid component in the liposomes is a lipid having two acyl groups, (i.e., diacylphosphatidylcholine and diacylphosphatidylethanolamine). Lipids having a variety of acyl chain groups of varying chain length and degree of saturation are available or may be isolated or synthesized by well-known techniques. In general, less saturated lipids are more easily sized, particularly when the liposomes must be sized below about 0.3 microns, for purposes of filter sterilization. In one group of embodiments, lipids containing saturated fatty acids with carbon chain lengths in the range of $C_{14}$ to $C_{22}$ are preferred. In another group of embodiments, lipids with mono or diunsaturated fatty acids with carbon chain lengths in the range of $C_{14}$ to $C_{22}$ are used. Additionally, lipids having mixtures of saturated and unsaturated fatty acid chains can be used. Liposomes useful in the present invention may also be composed of sphingomyelin or phospholipids with other head groups, such as serine and inositol. Still other liposomes useful in the present invention will include cholesterol, diglycerides, ceramides, phosphatidylethanolamine-polyoxyethylene conjugates or phosphatidic acid-polyoxyethylene conjugates. Methods used in sizing and filter-sterilizing liposomes are discussed below.

A variety of methods are available for preparing liposomes as described in, e.g., Szoka et al., *Ann. Rev. Biophys. Bioeng.* 9:467 (1980), U.S. Pat. Nos. 4,235,871, 4,501,728, 4,837,028, the text *Liposomes*, Marc J. Ostro, ed., Marcel Dekker, Inc., New York, 1983, Chapter 1, and Hope, et al., *Chem. Phys. Lip.* 40:89 (1986), all of which are incorporated herein by reference. One method produces multilamellar vesicles of heterogeneous sizes. In this method, the vesicle-forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder-like form. This film is covered with an aqueous buffered solution and allowed to hydrate, typically over a 15–60 minute period with agitation. The size distribution of the resulting multilamellar vesicles can be shifted toward smaller sizes by hydrating the lipids under more vigorous agitation conditions or by adding solubilizing detergents such as deoxycholate.

Following liposome preparation, the liposomes may be sized to achieve a desired size range and relatively narrow distribution of liposome sizes. A size range of about 0.2–0.4 microns allows the liposome suspension to be sterilized by filtration through a conventional filter, typically a 0.22 micron filter. The filter sterilization method can be carried out on a high through-put basis if the liposomes have been sized down to about 0.2–0.4 microns.

Several techniques are available for sizing liposomes to a desired size. One sizing method is described in U.S. Pat. No. 4,737,323, incorporated herein by reference. Sonicating a liposome suspension either by bath or probe sonication produces a progressive size reduction down to small unilamellar vesicles less than about 0.05 microns in size. Homogenization is another method which relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. In both methods, the particle size distribution can be monitored by conventional laser-beam particle size discrimination.

Extrusion of liposome through a small-pore polycarbonate membrane or an asymmetric ceramic membrane is also an effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve a gradual reduction in liposome size. For use in the present inventions, liposomes having a size of from about 0.05 microns to about 0.15 microns are preferred.

The compositions of the present invention are useful for the introduction of polyanionic materials into cells. Accordingly, the present invention also provides methods for introducing a polyanionic material into a cell. The methods are carried out in vitro by first contacting the polyanionic material with a composition of at least one neutral lipid and a cationic compound of formula I, to form a polyanionic material-liposome complex. After contacting the polyanionic material with the liposomal formulations to form a complex, the complex is then contacted with the cells for a period of time sufficient for transfection to occur.

In formula I, the symbols $R^1$, $R^2$, Y, Z, n, m, p, q, and $X^-$ are as described above for the compositions of the present invention. In one group of preferred embodiments, the cationic compounds used in the present methods are of formula I, wherein $R^1$ and $R^2$ are methyl and Y and Z are each independently —CH=CHCH$_2$CH$_2$CH$_2$—, —CH$_2$CH=CHCH$_2$CH$_2$—, —CH$_2$CH$_2$CH=CHCH$_2$— or —CH$_2$CH$_2$CH$_2$CH=CH—. In particularly preferred embodiments, $R^1$ and $R^2$ are methyl; Y and Z are each —CH=HCH$_2$CH$_2$CH$_2$—; n and q are both 7; and m and p are both 5. More preferably, the cationic compound is DODAC (N,N-dioleyl-N,N-dimethylammonium chloride). Other preferred embodiments for the method of the present invention will encompass the preferred compositions discussed above.

As noted above, the polyanionic material is first contacted with a composition comprising neutral lipids and cationic compounds to provide a polyanionic material-liposome complex. The contact can be made either prior to liposome formation (from the neutral lipids and cationic compounds) or subsequent to an initial liposome formation. In a preferred embodiment, liposomes of neutral lipids and the cationic compounds are formed first, then brought into contact with the polyanionic materials. The polyanionic materials will typically bind to the surface of the liposome as a result of the ionic attraction between the negatively charged polyanionic material and the positively charged surface of the liposome. Typically, the contact between the polyanionic material and the liposome which results in formation of a complex will be carried out at temperatures of from about 15° C. to about 45° C., preferably about 25° C. The length of time required to complete the formation of a complex will depend on the temperature as well as the nature of the polyanionic material and the liposome itself. When contact temperatures of about 25° C. are used, the length of time to form a complex between a liposome and a nucleic acid will be about 15 minutes to about 2 hours, however in some instances longer times may be required. Alternatively, the polyanionic materials can be incorporated into the interior of the liposomes by methods used for loading conventional drugs which are known to those of skill in the art. One method for loading drugs into liposomes involves encapsulation and can be carried out by a variety of techniques.

In one encapsulation technique, the drug and liposome components are dissolved in an organic solvent in which all species are miscible and concentrated to a dry film. A buffer is then added to the dried film and liposomes are formed having the polyanionic material incorporated into the vesicle walls. Alternatively, the polyanionic material can be placed into a buffer and added to a dried film of only lipid components. In this manner, the polyanionic material will become encapsulated in the aqueous interior of the liposome. The buffer which is used in the formation of the biologically come any biologically compatible buffer solution of, for example, isotonic saline, phosphate buffered saline, or other low ionic strength buffers. Generally, the polyanionic material will be present in an amount of from about 0.01 ng/mL to about 50 mg/mL. The resulting liposomes with the polyanionic material incorporated in the aqueous interior or in the membrane are then optionally sized as described above.

In one group of preferred embodiments, the polyanionic material:liposome complexes will have charge ratios (±) of from about 0.5 to about 4.0. To achieve these charge ratios, the complexes are formed by preparing an aqueous liposome formulation of the cationic lipid and at least one neutral lipid in which the cationic lipid is present in from about 25% to about 75% of the total lipid concentration. After sizing the liposomes, as discussed above, an aqueous solution of the polyanionic material is treated with the liposome suspension. The resulting preparation is then diluted, preferably about 5-fold, with a biologically compatible buffer to provide a final concentration of 0.05 to 1.0 µg/mL of the polyanionic material:liposome complex having a charge ratio of from about 0.5 to about 4.0.

Following formation of a polyanionic material:liposome complex, the complex is contacted with the cells to be transfected. Liposomes can be adsorbed to almost any cell type. Once adsorbed, the liposomes (including the complexes previously described) can either be endocytosed by a portion of the cells, exchange lipids with cell membranes, or fuse with the cells. Transfer or incorporation of the polyanionic portion of the complex can take place via any one of these pathways. In particular, when fusion takes place, the liposomal membrane is integrated into the cell membrane and the contents of the liposome combine with the intracellular fluid. Contact between the cells and the polyanionic material-liposome complex, when carried out in vitro, will take place in a biologically compatible medium. The concentration of lipid can vary widely depending on the particular application, but is generally between about 1 µmol and about 10 mmol. Treatment of the cells with the polyanionic materical:liposome complex will generally be carried out at physiological temperatures (about 37° C.) for periods of time of from about 1 to 6 hours, preferably of from about 2 to 4 hours. For in vitro applications, the delivery of polyanionic materials can be to any cell grown in culture, whether of plant or animal origin, vertebrate or invertebrate, and of any tissue or type. In preferred embodiments, the cells will be animal cells, more preferably mammalian cells, and most preferably human cells.

In one group of preferred embodiments, the polyanionic material:liposome complex is added to 60–80% confluent plated cells having a cell density of from about $10^3$ to about $10^5$ cells/mL, more preferably about $2 \times 10^4$ cells/mL. The concentration of the complex added to the cells is preferably of from about 0.01 to 0.2 µg/mL, more preferably about 0.1 µg/mL.

Typical applications include using well known transfection procedures to provide intracellular delivery of DNA or mRNA sequences which code for therapeutically useful polypeptides. However, the compositions can also be used for the delivery of the expressed gene product or protein itself. In this manner, therapy is provided for genetic diseases by supplying deficient or absent gene products (i.e., for Duchenne's dystrophy, see Kunkel, et al., *Brit. Med. Bull.* 45(3):630–643 (1989), and for cystic fibrosis, see Goodfellow, *Nature* 341:102–103 (1989)). Other uses for the compositions of the present invention include introduction of antisense oligonucleotides in cells (see, Bennett, et al., *Mol. Pharm.* 41:1023–1033 (1992)).

Alternatively, the compositions of the present invention can also be used for the transfection of cells in vivo, using methods which are known to those of skill in the art. In particular, Zhu, et al., *Science* 261:209–211 (1993), incorporated herein by reference, describes the intravenous delivery of cytomegalovirus (CMV)-chloramphenicol acetyltransferase (CAT) expression plasmid using DOTMA-DOPE complexes. Hyde, et al., *Nature* 362:250–256 (1993), incorporated herein by reference, describes the delivery of the cystic fibrosis transmembrane conductance regulator (CFTR) gene to epithelia of the airway and to alveoli in the lung of mice, using liposomes. Brigham, et al., *Am. J. Med. Sci.* 298:278–281 (1989), incorporated herein by reference, describes the in vivo transfection of lungs of mice with a functioning prokaryotic gene encoding the intracellular enzyme, chloramphenicol acetyltransferase (CAT).

When the polyanionic materials used in the present method are nucleic acids, they may be isolated from natural sources, obtained from such sources as ATCC or GenBank libraries or prepared by synthetic methods. Synthetic nucleic acids can be prepared by a variety of solution or solid phase methods. Generally, solid phase synthesis is preferred. Detailed descriptions of the procedures for solid phase synthesis of nucleic acids by phosphite-triester, phosphotriester, and H-phosphonate chemistries are widely available. See, for example, Itakura, U.S. Pat. No. 4,401, 796; Caruthers, et al., U.S. Pat. Nos. 4,458,066 and 4,500, 707; Beaucage, et al., *Tetrahedron Lett.*, 22:1859–1862 (1981); Matteucci, et al., *J. Am. Chem. Soc.*, 103:3185–3191 (1981); Caruthers, et al., *Genetic Engineering*, 4:1–17 (1982); Jones, chapter 2, Atkinson, et al., chapter 3, and Sproat, et al., chapter 4, in *Oligonucleotide Synthesis: A Practical Approach*, Gait (ed.), IRL Press, Washington D.C. (1984); Froehler, et al., *Tetrahedron Lett.*, 27:469–472 (1986); Froehler, et al., *Nucleic Acids Res.*, 14:5399–5407 (1986); Sinha, et al. *Tetrahedron Lett.*, 24:5843–5846 (1983); and Sinha, et al., *Nucl. Acids Res.*, 12:4539–4557 (1984) which are incorporated herein by reference.

The present invention is also useful for introducing other polyanionic materials into cells, particularly proteins. The introduction of exogenous or endogenous proteins into a cell can provide suitable therapy for an individual having cells which are unable to carry out translation of mRNA.

The following examples are offered solely for the purposes of illustration, and are intended neither to limit nor to define the invention.

EXAMPLES

Materials

Oleylamine was obtained from Fluka Chemical Company, St. Louis, Mo., USA. 40% Formaldehyde solution was obtained from Fischer Scientific, Ottawa, Canada. Sodium cyanoborohydride, stearyl bromide, oleic acid, oxalyl chloride, lithium aluminum hydride, methyl iodide and N-(2-hydroxyethyl)piperazine-N'-2-ethanesulfonic acid (HEPES) were obtained from Sigma Chemical Company, St. Louis, Mo., USA. N-(7-nitrobenz-2-oxa-1,3-diazol-4-yl) dioleoylphosphatidyl-ethanolamine (NBD-PE), N-(lissamine rhodamine 8 sulfonyl)dioleoylphosphatidyl-ethanolamine (Rho-PE) and 1,2-sn-dioleoylphoshatidyethanolamine (DOPE) were obtained from Avanti Polar Lipids, Alabaster, Ala., USA. The Lipex Extruder was obtained from Lipex Biomembranes, Vancouver, Canada. The pCMVβ expression vector (β-gal) was obtained from Clonetech Laboratories, Inc., Palo Alto, Calif., USA. Silica gel was obtained from BDH, Canada.

Methods

Lipofection

A general lipofection protocol was carried out as follows:

On Day 1, BHK cells were plated at $10^4$ cells/well of a 24-well plate in 0.5 mL of media (5% FBS in DMEM). On the second day, lipid:DNA complexes were prepared in 24-well plates by first dispensing $H_2O$ into the wells and then adding the lipid. The DNA was prepared in $H_2O$ and then added to the wells, agitated to mix and incubated at room temperature for 30 minutes. During the incubation period the media was removed from the cells and the cells were washed in PBS. After washing, 750 µL of SF-DMEM was added.

The lipid:DNA complexes (200 µL) were added to the appropriate wells containing the BHK cells and the plate was agitated to mix, then incubated at 37° C. for 4 hours. The transfection media was then replaced with 0.5 mL of 5% FBS in DMEM. On day 3, the media was removed and the cells were stained following standard procedure for the histochemical stain for β-galactosidase. On day 4, the stain was removed and the cells were washed with PBS, covered with 70% ethanol and counted.

Histochemical Staining For β-Galactosidase

The solutions required for histochemical staining include stock buffers, fixative, wash, and stain. These solutions were prepared and stored as follows:

1. Stock buffers were prepared as aqueous solutions using distilled, deionized water. Storage temperatures are as indicated. The solutions included: 47% glutaraldehyde, 4° C.; 1M $MgCl_2$, RT; 100 mM EGTA, pH 7.2, RT; 10% sodium deoxycholate, RT; 10% NP40, RT; 1M HEPES, 4° C.; 50 Mm $K_3Fe(CN)_6$, 4° C., stored in the dark for up to 3 months; 50 mM $K_4Fe(CN)_6$, 4° C., stored in the dark for up to 3 months; 5M NaCl, RT; and X-gal, a solid, was stored at −20° C.

2. The fixative solution had final concentrations of 0.2% glutaraldehyde, 2 mM $MgCl_2$ and 5 mM EGTA, and was prepared by combining 220 µL of 47% glutaraldehyde, 100 µL of $MgCl_2$ solution, and 2.5 mL of 100 mM EGTA at pH 7.2, and adjusting the total volume to 50 mL with PBS.

3. The wash solution was prepared by combining 100 µL of $MgCl_2$ solution, 500 µL of 10% sodium deoxycholate, and 100 µL of 10% NP40 and adjusting the total volume to 50 mL. This resulted in final concentrations of 2 mM $MgCl_2$, 0.1% sodium deoxycholate, and 0.02% NP40.

4. The stain was prepared by combining 2.2 mL of 1M HEPES, 3.0 mL of 50 mM $K_3Fe(CN)_6$, 3.0 mL of 50 mM $K_4Fe(CN)_6$, 150 µL of 5M NaCl, 65 µL of 1M $MgCl_2$ and $H_2O$ to provide a total volume of 50 mL. The solution was warmed to 42° C. and 12.5 mg of X-gal in 100 µL DMF (0.4% fmal volume) was added and dissolved. Alternatively, the X-gal can be made in DMF at 125 µg/µL and stored at −20° C. in foil. The final concentrations of the species in solution were 44 mM HEPES, 3 mM $K_3Fe(CN)_6$, 3 mM $K_4Fe(CN)_6$, 15 mM NaCl, 1.3 mM $MgCl_2$, and 0.5 mg/mL X-gal.

Cells were stained as follows:

The cells were washed once with PBS. Fixative (5 mL) was added to each plate and the cells were incubated at RT for five minutes. The fixative was removed and the cells were washed twice (3 minutes each) with permeabilization solution. X-gal stain (500 µL per well) was added to the cells which were then incubated overnight at 37° C. in an atmosphere of carbon dioxide. The pH of all of the solutions was maintained at 7.5–8.0 to avoid background interference from endogenous β-galactosidase.

Example 1

This example illustrates the synthesis of N-stearyl-N-oleyl-N,N-dimethylammonium chloride (OSDAC)

1.1 Synthesis of N,N-dimethyloleylamine

A solution of oleylamine (6.7 g) in acetonitrile (100 mL) and ethanol (50 mL) was treated with 40% aqueous formaldehyde (10 mL) and sodium cyanoborohydride (2.7 g) at room temperature for two hours. Acetic acid (5 mL) was slowly added and the solution stirred for an additional hour. The reaction mixture was then diluted with water, made basic with aqueous sodium hydroxide and extracted with methylene chloride, the organic fraction was dried over magnesium sulphate, filtered and the solvent was removed under vacuum. The residue was passed down a silica gel column (150 g) using 15% methanol in methylene chloride as the eluent, to provide a pale yellow oil.

1.2 Synthesis of OSDAC

A solution of N,N-dimethyloleylamine (1 g) and stearyl bromide (5.4 g) was dissolved in methylene chloride (50 mL) and treated with aqueous sodium hydroxide solution (5 mL of a 5M solution) at room temperature overnight with stirring. The reaction mixture was washed with water and then washed with dilute hydrochloric acid. The organic phase was washed with saturated sodium chloride solution (15x) and the solvent was removed. The residue was dissolved in methanolic hydrochloric acid and extracted from water and methylene chloride. This was repeated an additional three times. The organic solvent was then removed under vacuum and the residue passed down a silica gel column (150 g) using 5% methanol in methylene chloride as the eluent, to provide 0.6 g of OSDAC as a white powder after lyophilization from 10% methanol in benzene.

Example 2

This example illustrates the synthesis of N,N-dioleyl-N,N-dimethylammonium chloride (DODAC).

DODAC 2.1. Synthesis of N-oleoyloleylamide

A solution of oleic acid (5 g) in benzene (50 mL) was treated with oxalyl chloride (2 mL) at room temperature for one hour. The solvent and excess oxalyl chloride was removed under vacuum and the residue was dissolved in benzene (20 mL). A solution of oleylamine (7 g) in benzene (10 mL) was slowly added, followed by triethylamine (3 mL). The reaction mixture was stirred at room temperature for one hour and then neutralized with excess dilute hydrochloric acid. The mixture was extracted with methylene chloride and the combined organic extracts were dried over magnesium sulphate, filtered and the solvent was removed. The residue was passed down a silica gel column (150 g) using 5% methanol in methylene chloride as the eluent, to provide N-oleoyloleylamide as a white solid.

2.2. Synthesis of dioleylamine

A solution of N-oleoyloleylamide (prepared above) in THF (100 mL) was warmed to 40° C. Lithium aluminum hydride was slowly added until violent evolution of gas ceased. The reaction mixture was heated to reflux for one hour and then cooled to room temperature. Methanol (100 mL) was slowly added, followed by water (200 mL). Methylene chloride was added and the resultant suspension was stirred for fifteen minutes. The slurry was filtered and the precipitate was washed with ethanol\methylene chloride (50:50, 50 mL, 2x). The combined filtrates were washed with methylene chloride. The organic fraction was dried over magnesium sulphate, filtered and the solvent was removed under vacuum. The residue was passed down a silica gel column (150 g) using 5% methanol in methylene chloride as the eluent, to provide dioleylamine as a pale yellow oil.

2.3. Synthesis of N,N-dioleyl-N,N-dimethylammonium chloride

A solution of dioleylamine, prepared above, in chloroform (50 mL) was treated with methyl iodide (10 mL) at room temperature for one hour. Aqueous sodium hydroxide (1 mL of a 5M solution) and methyl iodide (5 mL) were then added and the mixture was stirred for an additional hour. The organic solvent was removed under vacuum and the resultant slurry was neutralized with dilute hydrochloric acid. Water was added and the reaction mixture was extracted with methylene chloride. The organic phase was washed with saturated sodium chloride solution (15x), after which the solvent was removed from the organic phase under vacuum. The residue was dissolved in a solution of concentrated hydrochloric acid in wet ethanol, diluted with water and extracted with methylene chloride. This process was repeated an additional three times. The product, after removal of solvent, was passed down a silica gel column (150 g) using methanol in methylene chloride as the eluent (5–32%). Pure fractions were combined and the solvent was removed, to provide N,N-dioleyl-N,N-dimethylammonium chloride (5 g) as a white waxy solid.

Example 3

This example illustrates the fusogenicity of cationic vesicle/DNA complexes with biomembranes.
3.1. Vesicle-vesicle fusion The vesicles used for these experiments were made by the extrusion procedure as previously described (see Hope, et al., *Biochim. Biophys. Acta* 812:55 (1985), incorporated herein by reference). Briefly, the cationic lipids mixtures, consisting of equal molar ratios of cationic lipid and DOPE, were dried down from chloroform under a stream of nitrogen gas. The residual solvent was removed under vacuum for two hours. The dry lipid film was hydrated in distilled water and the resulting multilamellar vesicle (MLV) suspension was freeze thawed five times using liquid nitrogen and warm water cycles. Large unilamellar vesicles were then formed by forcing the MLV suspension through two stacked 100 nm pore sized filters using the Lipex extruder.

Figure 1:
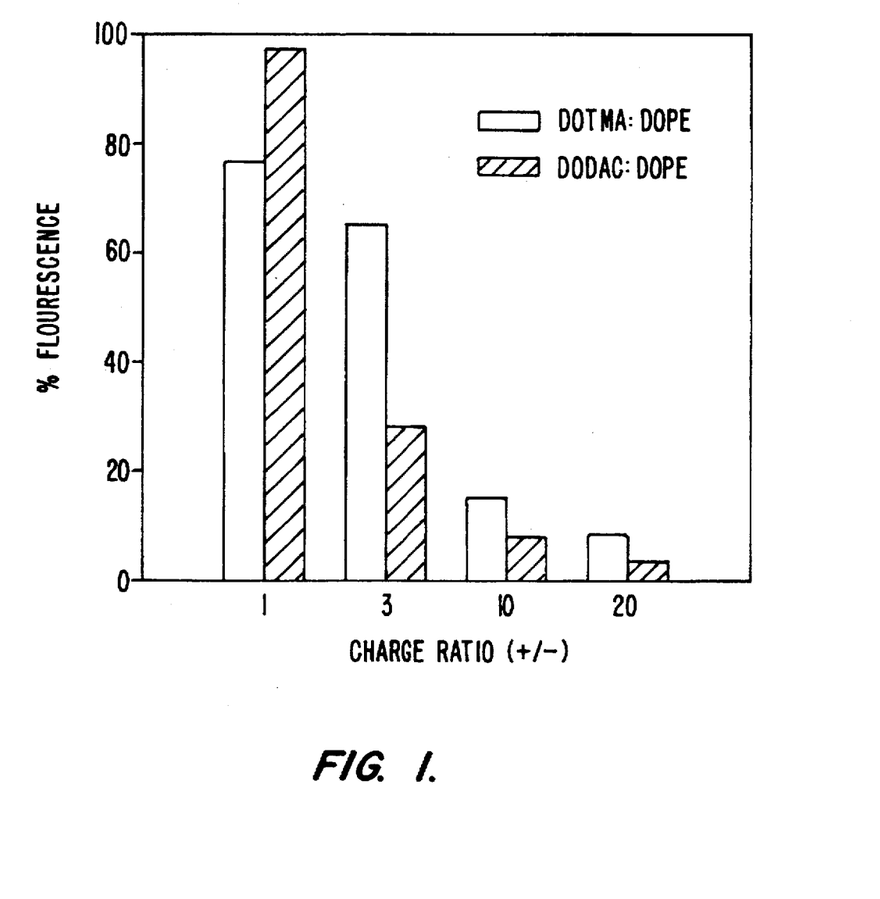
FIG. 1 illustrates the fusion of DOTMA:DOPE and DODAC:DOPE vesicles induced by plasmid DNA.

Vesicle fusion was monitored using resonance energy transfer as previously described in Struck, et al., *Biochemistry* 20:4093 (1981), incorporated herein by reference. Briefly, unlabelled vesicles were mixed 10:1 with similar vesicles obtaining 0.5 mole % of each of Rho-PE (N-(lissamine rhodamine B sulfonyl) dioleoylphosphatidylethanolamine) and NBD-PE (N-(7-nitrobenz-2-oxa-1,3-diazol-4-yl) dioleoylphosphatidylethanolamine) in 20 mM HEPES pH 7.4 buffer. The latter membrane fluorescent probe serves as the energy donor and the former as the energy acceptor. Fusion of labelled vesicles with unlabelled vesicles results in probe dilution. Thus, an increase in NBD-PE fluorescence due to a reduction of Rho-PE vesicles would be indicative of membrane fusion. A 7 kB β-gal plasmid was used to induce fusion of the cationic vesicles. FIG. 1 shows the results obtained from fusion experiments of DOTMA:DOPE and DODAC:DOPE with plasmid DNA. The charge ratios were calculated based on an average nucleotide molecular weight of 325. As FIG. 1 indicates, both DOTMA:DOPE and DODAC:DOPE vesicles fuse to a similar extent at all charge ratios and show optimal fusogenicity at a charge ratio of 1, which corresponds to the optimal charge ratio for transfection for both species (see FIG. 4).

3.2. Lipid-DNA complex fusion with Red Blood Cell (RBC) ghosts

Figure 2:
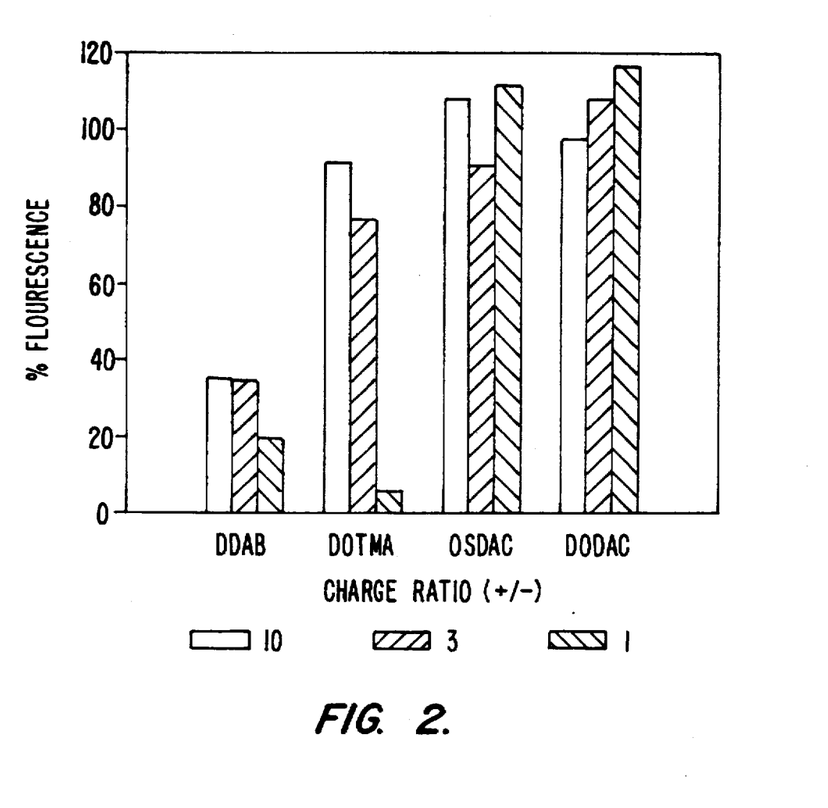
FIG. 2 illustrates the fusion of lipid/DNA complexes with RBC ghosts.

Cationic vesicles labelled with 0.5% each of Rho-PE and NBD-PE were mixed with a 7 kB β-gal plasmid in 20 mM HEPES pH 7.4 buffer. The lipid-DNA complex was then added to a solution of RBC ghosts. Fusion with the ghost membrane would result in probe dilution and an increase in NBD fluorescence. RBC ghosts were prepared as previously described in the literature (see, Wood, *Methods in Enzymology*, 149:271–280 Academic Press (1987)). FIG. 2 shows the results of lipid/DNA complex-RBC ghost fusion experiments using three different charge ratios and four different cationic lipids (DDAB, DOTMA, OSDAC, and

13

DODAC). As FIG. 2 illustrates, the unsaturated derivatives, DOTMA, DODAC and OSDAC, have superior fusion properties with respect to biological membranes than the saturated derivative, DDAB. In addition, DODAC and OSDAC show better fusogenic properties with RBC ghosts than DOTMA, which is the most commonly used commercial transfection lipid.

Example 4

This example provides one procedure whereby BHK cells can be transfected using a β-gal plasmid. The general protocol followed is provided in the Methods section above.

Figure 3:
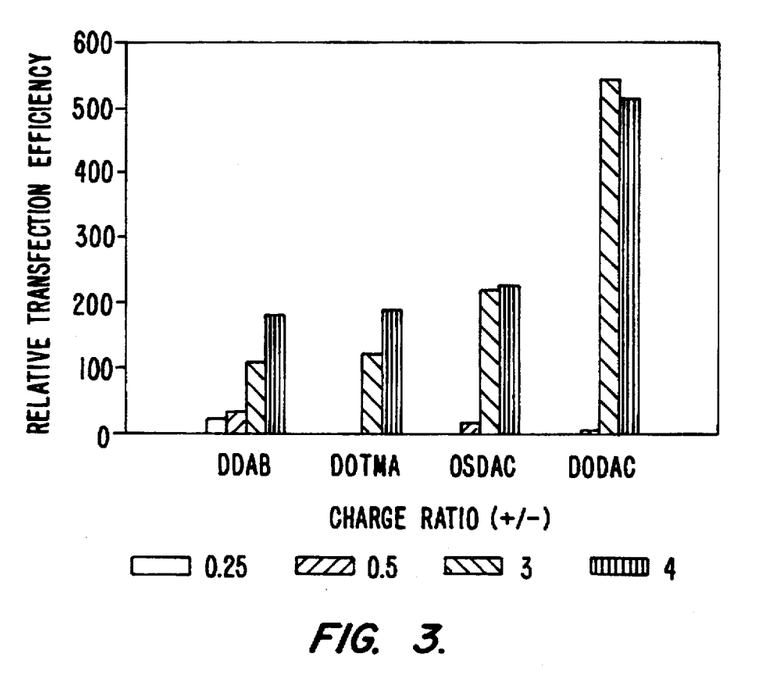
FIG. 3 illustrates a preliminary survey of the transfection abilities of cationic lipid vesicles formulated with 50 mole % DOPE.

FIG. 3 provides a survey of the relative transfection efficiencies of four lipids, DDAB, DOTMA, OSDAC and DODAC at four charge ratios (0.25, 0.5, 3 and 4). The relative transfection efficiency is the average number of transfected cells for 25 arbitrary areas on the cell plate. DODAC shows significantly better relative transfection efficiencies at charge ratios in excess of 1, whereas DDAB, DOTMA and OSDAC are all similar. All preparations have low transfection efficiencies below a charge ratio of 1. The comparison between DDAB and DODAC is particularly important as it demonstrates the effect of unsaturation on transfection efficiency.

Figure 4:
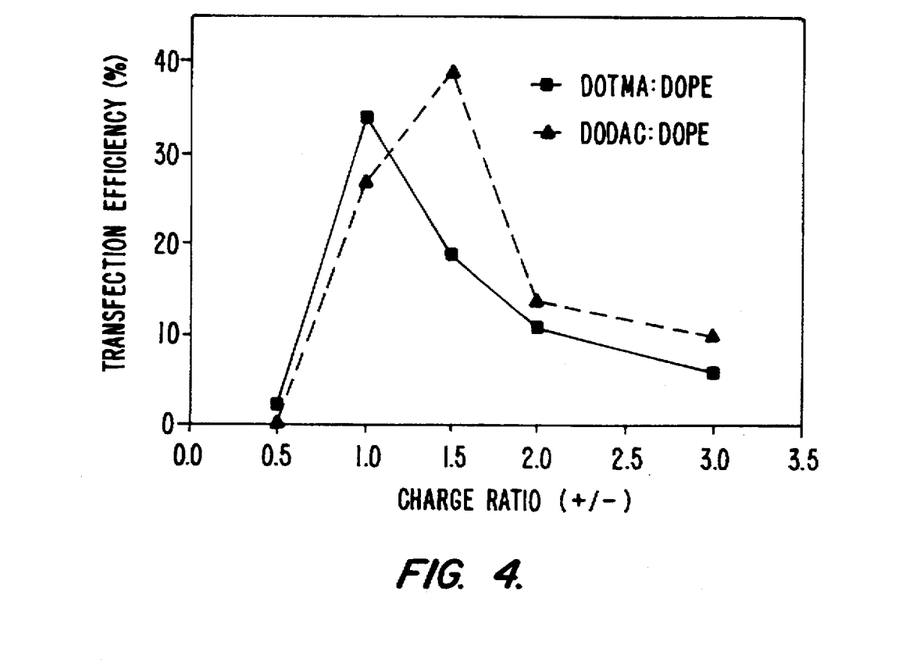
FIG. 4 illustrates the charge ratio titration of DOTMA:DOPE and DODAC:DOPE transfection efficiencies in BHK cells.

The transfection efficiency, expressed in terms of the number of transfected cells over the total number of cells, of DODAC and DOTMA at various charge ratios is shown in FIG. 4. Optimal transfection for both systems occurs for charge ratios between 1 and 2, and levels off at higher charge ratios. The transfection efficiency at charge ratios below 1 are markedly lower, consistent with the results presented in FIG. 3.

All publications, patents and patent applications mentioned in this specification are herein incorporated by reference into the specification to the same extent as if each individual publication, patent or patent application was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

What is claimed is:

1. A method for introducing a polyanionic material into a cell comprising;

(a) contacting said polyanionic material with a composition comprising a cationic compound of formula I:

wherein
  $R^1$ and $R^2$ are each independently $C_1$ to $C_3$ alkyl;
  Y and Z are each independently members selected from the group consisting of —$CH_2CH_2CH_2CH_2CH_2$—, —$CH=CHCH_2CH_2CH_2$—, —$CH_2CH=CHCH_2CH_2$—, —$CH_2CH_2CH=CHCH_2$—, —$CH_2CH_2CH_2CH=CH$—, —$CH=CHCH=CHCH_2$—, —$CH=CHCH_2CH=CH$—, and —$CH_2CH=CHCH=CH$—, with the proviso that Y and Z are not both —$CH_2CH_2CH_2CH_2CH_2$;
  n and q are independently integers of from 3 to 7; and
  m and p are independently integers of from 4 to 9, with the proviso that the sums n+m and q+p are each integers of from 10 to 14; and
  $X^-$ is a member selected from the group consisting of pharmaceutically acceptable anions of organic and inorganic acids;
and at least one neutral lipid to form a polyanionic material-liposome complex; and (b) contacting said polyanionic material-liposome complex with a cell for a period of time sufficient for said polyanionic material to be introduced into said cell.

2. The method of claim 1 wherein said polyanionic material is a member selected from the group consisting of DNA, RNA and a protein.

3. The method of claim 1 wherein said polyanionic material is a member selected from the group consisting of DNA and RNA, $R^1$ and $R^2$ are methyl, Y and Z are independently members selected from the group consisting of —$CH=CHCH_2CH_2CH_2$—, —$CH_2CH=CHCH_2CH_2$—, —$CH_2CH_2CH=CHCH_2$— and —$CH_2CH_2CH_2CH=CH$—, and said neutral lipid is a member selected from the group consisting of diacylphosphatidylcholine, diacylphosphatidylethanolamine, ceramide and sphingomyelin.

4. The method of claim 1 wherein said polyanionic material is a member selected from the group consisting of DNA and RNA, $R^1$ and $R^2$ are methyl, Y and Z are both —$CH=CHCH_2CH_2CH_2$—, n and q are both 7, m and p are both 5, and said neutral lipid is 1,2-sn-dioleoylphosphatidylethanolamine.

* * * * *